(12) United States Patent
Coe

(10) Patent No.: US 7,338,433 B2
(45) Date of Patent: Mar. 4, 2008

(54) REMOTELY ADJUSTABLE GASTRIC BANDING METHOD

(75) Inventor: Frederick L. Coe, Santa Barbara, CA (US)

(73) Assignee: Allergan, Inc., Irvine, CA (US)

(*) Notice: Subject to any disclaimer, the term of this patent is extended or adjusted under 35 U.S.C. 154(b) by 24 days.

(21) Appl. No.: 10/524,864

(22) PCT Filed: Aug. 13, 2002

(86) PCT No.: PCT/US02/25654

§ 371 (c)(1), (2), (4) Date: Jun. 23, 2005

(87) PCT Pub. No.: WO2004/014245

PCT Pub. Date: Feb. 19, 2004

(65) Prior Publication Data

US 2005/0250979 A1 Nov. 10, 2005

(51) Int. Cl.
*A61F 2/02* (2006.01)
(52) U.S. Cl. ..................................................... 600/31

(58) Field of Classification Search ............ 600/29–32, 600/37; 604/149, 909, 97.01, 98.01, 99.01; 128/847, 899; 623/23.65, 23.67, 23.68
See application file for complete search history.

(56) References Cited

U.S. PATENT DOCUMENTS

| | | | | |
|---|---|---|---|---|
| 5,928,195 A | * | 7/1999 | Malamud et al. ............ 604/141 |
| 5,938,669 A | * | 8/1999 | Klaiber et al. .............. 606/157 |
| 5,944,751 A | * | 8/1999 | Laub ........................... 623/2.1 |
| 6,067,991 A | | 5/2000 | Forsell |
| 6,102,922 A | | 8/2000 | Jakobsson et al. |
| 6,210,347 B1 | | 4/2001 | Forsell |
| 6,432,040 B1 | * | 8/2002 | Meah .......................... 600/37 |
| 6,450,946 B1 | | 9/2002 | Forsell |
| 6,457,801 B1 | * | 10/2002 | Fish et al. .................... 347/19 |

* cited by examiner

*Primary Examiner*—Charles A. Marmor, II
*Assistant Examiner*—Christine Hopkins
(74) *Attorney, Agent, or Firm*—Debra D. Condino; Martin A. Voet

(57) ABSTRACT

A remotely controllable gastric banding device (10) for placement around the stomach of a patient for the treatment of obesity. The device (10) comprises a gastric band (10) having an inflatable chamber (16) for adjusting the inner circumference of the band (10), a pressurized reservoir (20) with a valve (31) for providing fluid to inflate the inflation chamber (16), a valve (32) for releasing fluid from the inflatable chamber (16), and a controller (41) for controlling the valves (31, 32). The controller (41) is remotely controllable from outside the patient.

24 Claims, 2 Drawing Sheets

REMOTELY ADJUSTABLE GASTRIC BANDING METHOD

BACKGROUND OF THE INVENTION

1. Field of the Invention

The present invention relates generally to an apparatus for remotely adjusting the volume in the inflatable portion of a surgically implanted gastric band encircling the stomach. A method for treating morbid obesity utilizing a remotely adjustable gastric banding device is also disclosed.

2. Description of the Related Art

A belt-like gastric band for encircling the stomach to control morbid obesity is disclosed by Vincent in U.S. Pat. No. 5,601,604, incorporated herein by reference. The band comprises a belt that can be passed around the stomach and locked into an encircling position in order to create a stoma opening within the stomach. An adjustable portion of the band comprises an inflatable member which permits fine adjustment of the stoma opening after the stoma is created by locking the band in place.

The gastric banding procedure may involve placement of a calibrating apparatus in the stomach to position the stoma and size the pouch created above the stoma. The gastric band is fastened in position about the stomach to prevent slippage, usually by gastro-gastric sutures.

The stoma opening may be adjusted by injecting or withdrawing a fluid into or from an inflatable member, which is preferably coextensive with a portion of the inner stomach-contacting surface of the band. The means for injecting the fluid into the inflatable member usually comprises a fill port located beneath the skin that can be accessed extracorporeally by transdermal injection. Thus, following implantation, the gastric band can be adjusted to enlarge or reduce the stoma as required.

A potential disadvantage of prior art gastric bands is the difficulty in finely adjusting the stoma created by the implanted band. For example, the fill port located beneath the skin can be difficult to locate precisely. In addition, the fill procedure requires an invasive transdermal injection to adjust the band. Hence, repeated adjustments may be painful or worrisome to the patient. Moreover, exposure to x-rays may be required to facilitate location of the port. It would therefore be desirable to provide a band having an inflatable member that can be easily, precisely, and readily adjusted remotely, without the need to undergo an invasive procedure or radiographic exposure.

To address this problem, several prior art remote control gastric banding devices have been proposed. Klaiber et al. (U.S. Pat. No. 5,938,669) discloses a radio controlled gastric band adjusted by means of an electric pump and a balancing reservoir. Forsell (U.S. Pat. No. 6,210,347) discloses a remotely controlled and powered gastric band adjusted by a motorized mechanical or hydraulic means. Each of these proposed devices operates by pumping fluid to or from the gastric band. Unfortunately, because of their energy requirements, these devices pose problems for practical use. These devices are also not suitable for use with existing gastric banding systems, such as that disclosed by Vincent.

Recent developments in implantable drug delivery devices have shown that small, reliable, and energy-efficient implantable devices are feasible. Drug delivery devices currently exist in which drugs are administered periodically or continuously to a patient having an implanted device by applying pressure from a pressurized reservoir and opening an outlet valve to allow a pressure differential to cause a flow of the drug. For example, Malamud et al. (U.S. Pat. No. 5,928,195) discloses a remotely controlled drug delivery device suitable for implantation in a body cavity. A pressurized gas chamber presses upon a drug storage chamber thereby administering a dose of the drug when a valve is remotely opened.

Similarly, Arzbaecher (U.S. Pat. No. 5,607,418) discloses an implantable drug apparatus having nested deformable chambers with the outer chamber being pressurized. The pressure from the outer pressurized chamber forces the drug from a reservoir chamber into an inner dispensing chamber. A remotely controlled valve is used to administer a dose of the drug from the dispensing chamber. Further, Haller et al. (U.S. Pat. No. 6,203,523) discloses an implantable drug infusion device having a flow regulating mechanism that permits the flow rate to be independent of reservoir pressure. Some of the tradeoffs between "passive" (pressurized reservoir-based) devices and "active" (pump-based) devices are discussed in Haller, the disclosure of which is incorporated herein by reference.

OBJECTS OF THE INVENTION

The foregoing demonstrates a need for a practical, accurate and easy means of remotely adjusting an implanted gastric band.

It is therefore an object of the present invention to provide a practical, accurate and efficient means for remotely adjusting an implanted gastric band.

It is another an object of the present invention to remotely adjust an implanted gastric band having an inflatable member.

It is yet another object of the invention to provide a remote control means suitable for use with existing gastric banding devices and technology.

Still another an object of the present invention is to minimize device complexity for an implanted remotely adjustable gastric banding device to ensure maximum device longevity/durability, in light of the fact that repair would require additional surgery.

Various other objects, advantages and features of the present invention will become readily apparent from the ensuing detailed description and the novel features will be particularly pointed out in the appended claims.

SUMMARY OF THE INVENTION

The present invention applies recent developments in implantable drug delivery device technology to the field of gastric banding.

A preferred embodiment of the invention provides a gastric banding device for treatment of morbid obesity. The device has a gastric band suited for laparoscopic placement around the stomach of a patient to form an adjustable stoma opening. The gastric band has an inflatable chamber for adjusting the inner circumference of the band. The inflatable chamber is preferably substantially coextensive with an inner stomach-facing surface of the gastric band. The inflatable member does not wrinkle or fold when adjusted, thereby presenting a substantially smooth contour along the inner circumference. A fluid-filled pressurized reservoir provides a source of fluid to inflate the inflation chamber of the gastric band. First and second valves control the flow between the pressurized reservoir, the inflatable chamber, and an unpressurized or negatively pressurized outlet. A controller is used to control the valves, thereby regulating the volume change in the inflatable chamber to adjust the inner circumference of the band. The controller is remotely controllable from outside of the patient.

Other aspects of the invention include a remote control for remotely transmitting control signals to the controller, a receiver for receiving control signals from the remote control, and a power source for providing power to the controller and the valves. The power source may be an induction coil. The power source may also be a battery or capacitor charged by a piezoelectric device which converts body motion into electrical energy.

In a method according to the invention, a remotely adjustable gastric banding system may be use for the treatment of obesity. The method comprises the steps of implanting a gastric band, preferably laparoscopically, around the stomach of the patient to create a stoma; remotely transmitting control signals from outside of the patient to a controller of the implanted gastric banding device; and actuating a first valve, between a pressurized reservoir and an inflatable chamber, and/or a second valve, between the inflatable chamber and an outlet, on the basis of the control signals received by the controller to increase or decrease the fluid volume in the inflatable chamber, thereby adjusting the inner circumference of the band to adjust the stoma.

BRIEF DESCRIPTION OF THE DRAWINGS

The following detailed description given by way of example, but not intended to limit the invention solely to the specific embodiments described, may best be understood in conjunction with the accompanying drawings in which.

DETAILED DESCRIPTION OF CERTAIN PREFERRED EMBODIMENTS

The present invention combines the implantable drug delivery device technology discussed above with gastric banding technology. The preferred embodiments of the apparatus and method according to the present invention will be described with reference to the accompanying drawings.

Figure 1:
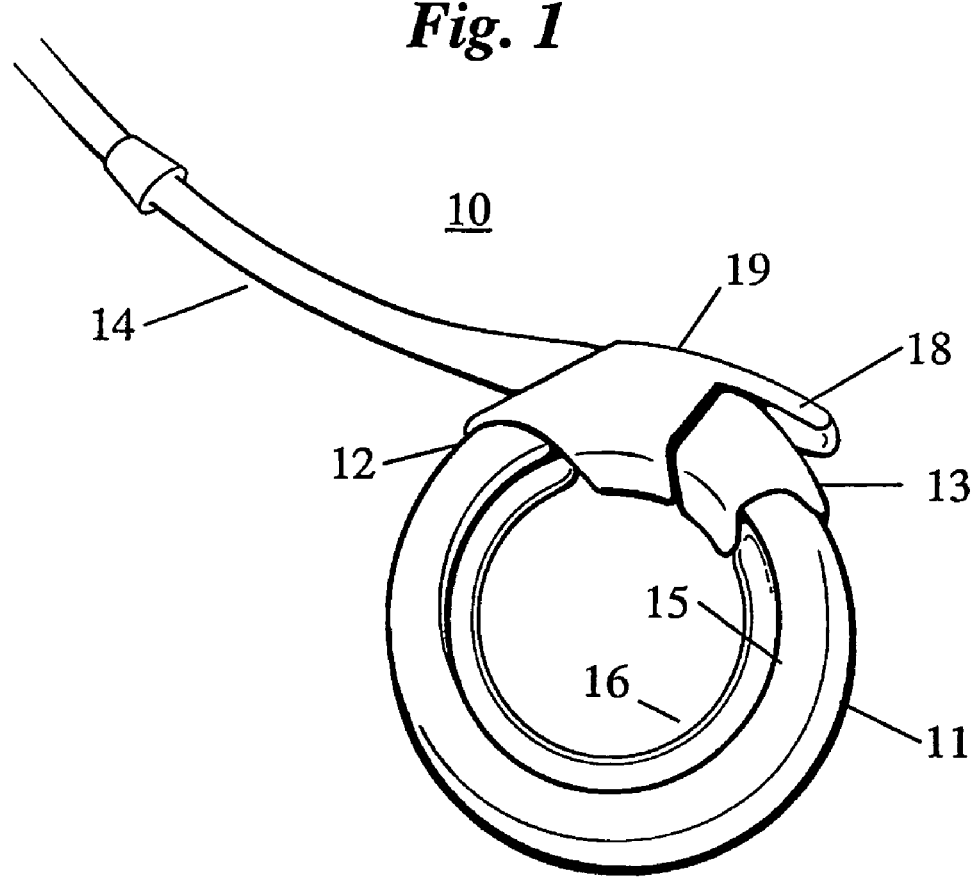
FIG. 1 is a perspective view of a laparoscopically implantable gastric band, which may be used in the present invention, fastened in an encircling position and partially inflated.

Referring to FIG. 1, a gastric band for use with the present invention is disclosed in Vincent (U.S. Pat. No. 5,601,604). This compatible gastric band, indicated as reference numeral 10, has a body portion 11 with an inner stomach-facing surface 15. The body portion 11 has a head end 12 and a tail end or "belt" 13. A fill tube 14, which is generally a tube having a single lumen coextensive therewith, is in fluid communication with an inflatable chamber 16 on the inner surface 15 of the band body 11. Preferably, the inflatable portion 16 is substantially coextensive with the inner surface 15 of the body portion 11. The central lumen of the fill tube 14 is in fluid communication with inflatable chamber 16. The head end 12 of the body portion 11 has a "buclde" 19 through which the tail end of "belt" 13 is inserted and locked in place in use. Head end 12 may be provided with a pull tab 18 for use in locking the band in place about the stomach.

Figure 2:
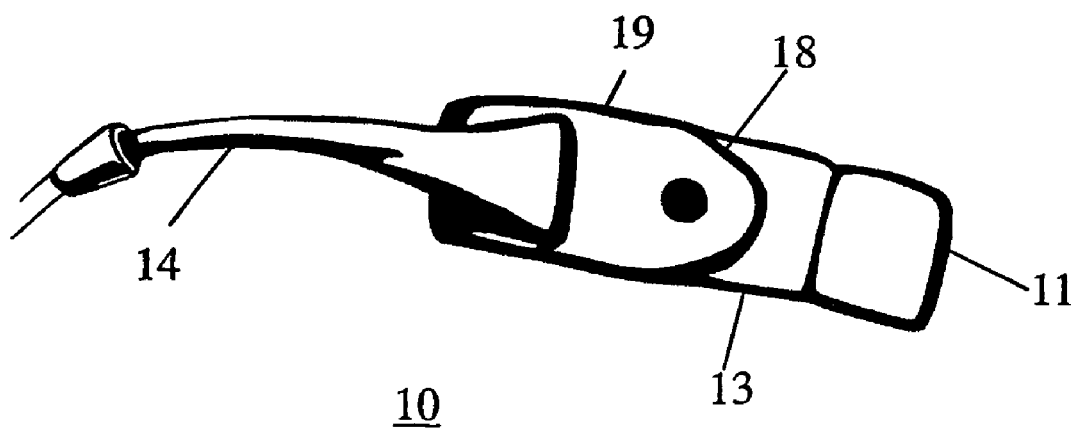
FIG. 2 is a side view of the gastric band shown in FIG. 1.

In use, the gastric band is placed in an encircling position around the stomach and locked in place as shown in FIG. 2. (In FIG. 2, the stomach is omitted for clarity.) This is accomplished by introducing the gastric band 10 through a laparoscopic cannula (not shown) in a patient's abdominal cavity. Laparoscopic placement consists of blunt dissection below the gastro-esophageal junction followed by placement of the band. The end of the fill tube 14 is passed through the dissected path around the upper stomach, and the tail end or belt 13 is passed through buckle 19, so that the belt and buckle lock in place. A laparoscopic closure tool, such as that disclosed by Coe and Vincent in U.S. Pat. No. 5,658,298, incorporated herein by reference, may be used. Hence, with the gastric band affixed in an encircling position around the stomach, a new stoma (opening) is created within the stomach. After the band is secured in position, the size of the stoma may be adjusted by adding fluid to or withdrawing fluid from the inflatable member 16 to bring the stoma opening to the desired size. The inflatable member or chamber 16 is preferably coextensive with the inner stomach-facing surface 15 of the band between the head end 12 and the tail end 13. The interior of the adjustable chamber 16 is in fluid communication with a fluid reservoir (not shown) by means of the central lumen of the fill tube 14, as with prior art adjustable gastric bands. The inflatable member 16 is gradually inflated or deflated with saline or other biologically compatible fluid via the fluid reservoir such that the inflatable member 16 presses on and constricts the stomach wall or other tissue underlying the band. This results in the decrease or increase of the size of the stomach opening directly inside the encircling band.

Figure 3:
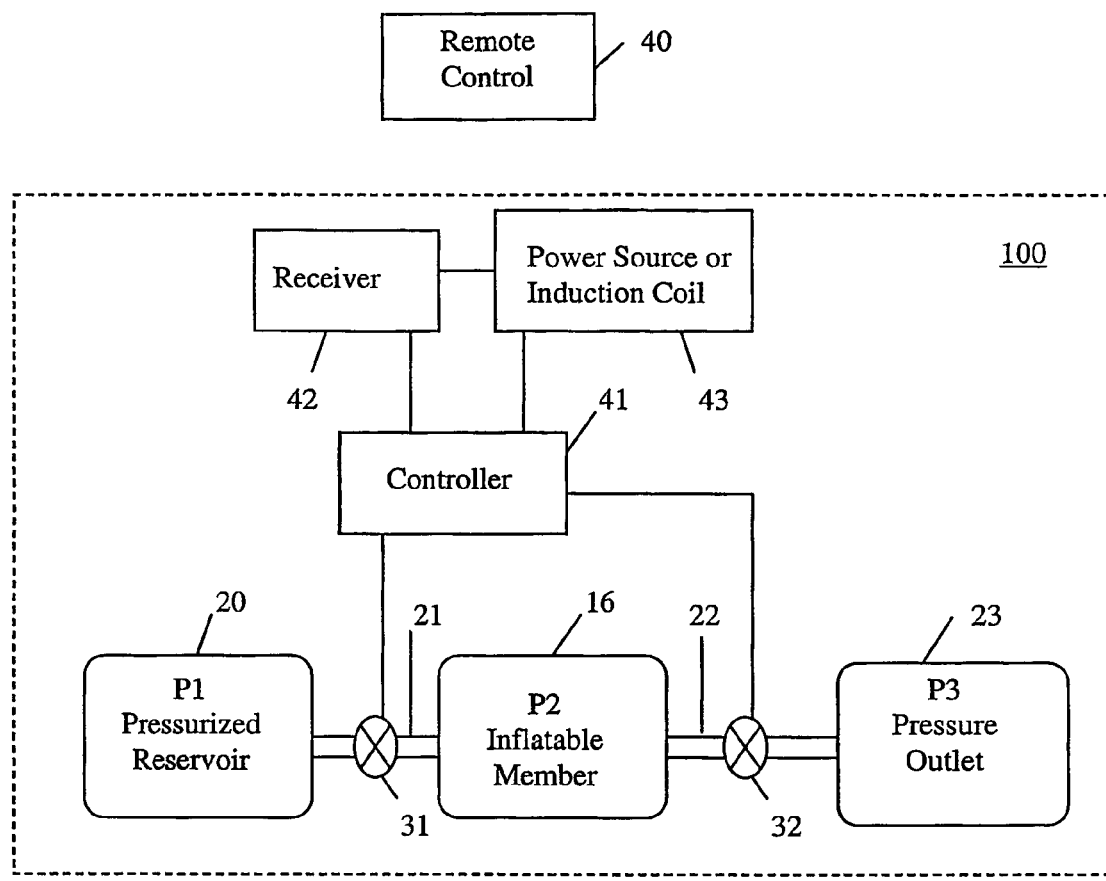
FIG. 3 is a schematic diagram showing a remotely controlled fluid distribution system for a gastric band according to the present invention.

FIG. 3 is a schematic diagram depicting a remotely adjustable gastric band 100 constructed in accordance with the present invention. In FIG. 3, the pressure in the inflatable member 16 of the remote gastric banding system 100 is represented by the band inflation pressure P2. Pressure P2 is regulated by an inlet valve 31 and an outlet valve 32. Pressurized reservoir 20, having a pressure P1, is connected to the inflatable chamber 16 through inlet valve 31 and tube 21, which corresponds to fill tube 14 in FIG. 2. Pressurized reservoir 20 is analogous to the pressurized reservoirs discussed above in relation to implantable drug delivery devices. This reservoir may be connected to the fill tube 21 as shown, or it may be incorporated into the body 11 of the band itself, e.g. on the outer surface, opposite the inner stomach-facing surface 15, and communicate directly with inflatable chamber 16 though inlet valve 21. Inflatable member 16 is also connected to outlet 23, having a pressure P3, through tube 22 and valve 32. Outlet 23 may be either a separate waste reservoir as shown in FIG. 3 or the peritoneal cavity of the patient's body. When outlet 23 is a waste reservoir, P3 may be negative. Where pressure outlet 23 is the patient's peritoneal cavity, P3 will be at ambient pressure within the body.

In the present invention, the pressure relationship between reservoir 20, inflatable member 16 and outlet 23 is initially represented by the formula P1>P2>P3. Hence, valve 31 may be used to increase the pressure P2 up to a maximum pressure of P2=P1, thereby inflating inflatable member 16. Similarly, valve 32 may be used to decrease the pressure P2 down to a minimum of P2=P3, thereby deflating inflatable member 16. Thus, by actuating valves 31 and 32, the fluid volume in the inflatable member 16 may be regulated, thereby adjusting the size of the stoma formed by the gastric band.

In the present invention, valves 31 and 32 are controlled by a controller 41. The valves are preferably controlled in accordance with externally transmitted signals (not shown) received by a receiver 42 but may ultimately be controlled by any control system, including internal, mechanical, wired, or the like. The signals are preferably radio frequency (RF) signals transmitted by a remote control device 40 located external to the implanted gastric banding system. Power may be supplied to the receiver, the controller, and/or the valves either from an implanted power source 43 or from an induction coil 43 that receives power from a concentric coil external to the body, as described for instance for hearing aids in Baumann et al. (U.S. Pat. No. 5,279,292), which is hereby incorporated by reference.

The entirety of the remote gastric banding system 100 shown in FIG. 3 may be laparoscopically implanted in the patient. Subsequent adjustment of the band can be simply, quickly, and painlessly performed using a remote control device to remotely inflate/deflate the inflatable portion 16 of the band. The entire system 100 may be removed from the patient if necessary. No permanent anatomical changes should be anticipated.

The remote control device 40 can be in the form of a typical television remote control, a personal computer interfaced device, or any other format. A unique identification code may be assigned to each remotely adjustable gastric band, so that access to and control of the device is restricted. This code may be a PIN code and may also act to prevent accidental adjustment of the band.

The system may be pressurized using a saline solution, or any other biocompatible fluid. If desired, a concentrated saline solution may be used as the inflation medium, thereby allowing water from the patient's body to diffuse into the inflatable member 16 over time and further inflate the band. After repeated adjustments the reservoir 20 may be refilled through an access port (not shown) or replaced altogether. As a backup and safety measure, the system may also allow for inflation/deflation of inflatable member 16 by transdermal injection through a fill port (not shown) as in prior art gastric banding devices.

Because this system uses a pressurized reservoir rather than a mechanical pressurization means (i.e. a pump or screw), the present system is more energy-efficient than those disclosed in the existing remote-controlled adjustable gastric band systems of Klaiber or Forsell (U.S. Pat. Nos. 5,938,669 and 6,210,347). Power is only required when operating the valves 31 and/or 32, and then only for relatively short time intervals.

Alternative embodiments of the present invention may include means for measuring fluid flow through the valves 31 and/or 32, such as a mass flowmeter, to ensure accuracy in adjusting the stoma when inflatable member 16 is inflated or deflated. Also, the controller 41 may be positioned external to the body. An alternate gastric band design might also be used, provided that the inflation medium remains a fluid.

A further embodiment of the present invention is a method of treating obesity using the remotely adjustable gastric banding system disclosed herein. The method includes implanting a gastric band, preferably laparoscopically, around the stomach of the patient to create a stoma; remotely transmitting control signals from outside of the patient to controller 41 of the gastric banding device inside of the patient; and opening and closing valve 31, between pressurized reservoir 20 and inflatable chamber 16, and/or valve 32, between the inflatable chamber and outlet 23, on the basis of the control signals received by controller 23 to increase or decrease the pressure in the inflatable chamber, thereby adjusting the inner circumference of the band to adjust the stoma size.

Although the invention has been particularly shown and described with reference to certain preferred embodiments, it will be readily appreciated by those of ordinary skill in the art that various changes and modifications may be made therein, without departing from the spirit and scope of the invention. It is intended that the claims be interpreted as including the foregoing as well as various other such changes and modifications.

What is claimed is:

1. A method of treating obesity in a patient, comprising the steps of:
   implanting a gastric banding device around the stomach of the patient to create a stoma; said gastric banding device having an inflatable chamber;
   remotely transmitting control signals from outside of the patient to a controller of the gastric banding device inside of the patient; and
   actuating a first valve, between a pressurized fluid reservoir and said inflatable chamber, or a second valve, between said inflatable chamber and an outlet, on the basis of the control signals received by the controller to increase or decrease the fluid volume in said inflatable chamber, wherein the pressure in said pressurized fluid reservoir remains greater than or equal to the pressure in said inflatable chamber, thereby adjusting an inner circumference of the band.

2. The method according to claim 1, wherein the control signals are remotely transmitted using a remote control.

3. The method according to claim 1, wherein the controller has a receiver for receiving the control signals.

4. The method according to claim 1, wherein said inflatable chamber is substantially coextensive with an inner stomach-facing surface of said gastric banding device.

5. The method according to claim 1, wherein said gastric banding device forms a smoothly surfaced circle.

6. The method according to claim 1, wherein the control signals are RF signals and the method further comprises operating a remote control to remotely transmit control signals to the controller.

7. The method according to claim 6, wherein the remote control is a handheld device.

8. The method according to claim 6, wherein the remote control is a computer.

9. The method according to claim 1, wherein the control signals are RF signals, and the controller has a unique identification code assigned thereto, wherein the step of remotely transmitting control signals from outside of the patient comprises first entering the unique identification code.

10. The method according to claim 1, further comprising a power source for providing power to the controller, the first valve, and the second valve, selected from the group consisting of:
    an induction coil;
    a battery; and
    a capacitor.

11. The method according to claim 1, further comprising a piezo-electrically charged capacitor for providing power to the controller, the first valve, and the second valve.

12. The method according to claim 1, wherein a pressure P1 within the pressurized fluid reservoir is initially greater than a pressure P2 in the inflatable chamber, and P2 is initially greater than a pressure P3 at the outlet, wherein the step of actuating the first valve reduces P1 in favor of P2, and the step of actuating the second valve reduces P2 in favor of P3.

13. The method according to claim 1, wherein the outlet is in fluid communication with the peritoneal cavity of the patient, and the step of actuating the second valve releases fluid volume from within the inflatable chamber to the peritoneal cavity.

14. The method according to claim 1, wherein the outlet is a waste reservoir, and the step of actuating the second valve releases fluid volume from within the inflatable chamber to the waste reservoir.

15. The method according to claim 1, wherein the step of implanting comprises laparoscopic placement of the gastric banding device.

16. The method according to claim 15, wherein the gastric banding device comprises a body portion with a head end having a buckle and a tail end, wherein the step of implanting includes inserting the tail end into the buckle of the head end and locking the tail end in place within the buckle.

17. The method according to claim 16, wherein the gastric banding device further comprises a pull tab on the head end, wherein the step of locking the tail end in place within the buckle is done by pulling the pull tab.

18. The method according to claim 1, wherein the gastric banding device comprises a band body with an inner stomach-facing surface, and the inflatable chamber is located on the inner stomach-facing surface of the band body.

19. The method according to claim 18, wherein the fluid reservoir is located on the outer stomach-facing surface of the band body opposite the inner stomach-facing surface.

20. The method according to claim 1, wherein the band body comprises a head end having a buckle and a tail end, and a fill tube connected to the tail end to which the fluid reservoir is connected.

21. The method according to claim 1, further including a fill port and fill tube connected to the gastric banding device and in fluid communication with the inflatable chamber, the method further including adjusting the fluid volume within the inflatable chamber from outside the body by transdermal injection through the fill port.

22. The method according to claim 1, further including an access port in fluid communication with the fluid reservoir, the method further including refilling the fluid reservoir from outside the body through the access port.

23. The method according to claim 1, further including replacing the fluid reservoir.

24. The method according to claim 1, further including measuring fluid flow through the first valve.

* * * * *

UNITED STATES PATENT AND TRADEMARK OFFICE
CERTIFICATE OF CORRECTION

| | |
|---|---|
| PATENT NO. | : 7,338,433 B2 |
| APPLICATION NO. | : 10/524864 |
| DATED | : March 4, 2008 |
| INVENTOR(S) | : Coe |

It is certified that error appears in the above-identified patent and that said Letters Patent is hereby corrected as shown below:

In column 3, line 61, delete ""buclde"" and insert -- "buckle" --, therefor.

Signed and Sealed this

Seventeenth Day of June, 2008

JON W. DUDAS
*Director of the United States Patent and Trademark Office*